(12) United States Patent
Yamamoto et al.

(10) Patent No.: US 7,335,496 B2
(45) Date of Patent: Feb. 26, 2008

(54) METHOD FOR PRODUCING TARGET SUBSTANCE

(75) Inventors: Yoko Yamamoto, Kawasaki (JP); Hisao Ito, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 435 days.

(21) Appl. No.: 10/859,210

(22) Filed: Jun. 3, 2004

(65) Prior Publication Data

US 2005/0170474 A1   Aug. 4, 2005

(30) Foreign Application Priority Data

Jun. 5, 2003  (JP) ............................ 2003-161181

(51) Int. Cl.
*C12P 19/40*   (2006.01)
(52) U.S. Cl. .................... 435/88; 435/89; 435/106; 435/108; 435/488
(58) Field of Classification Search ............... None
See application file for complete search history.

(56) References Cited

U.S. PATENT DOCUMENTS

| 2001/0049126 A1 | 12/2001 | Livshits et al. ............. 435/106 |
| 2002/0160461 A1 | 10/2002 | Nakai et al. .................... 435/89 |
| 2003/0077764 A1 | 4/2003 | Tsujimoto et al. .......... 435/106 |
| 2004/0121428 A1 | 6/2004 | Sugimoto et al. .......... 435/69.1 |

FOREIGN PATENT DOCUMENTS

| AU | 199719218 B2 | 9/1997 |
| EP | 0 839 909 A1 | 5/1996 |
| EP | 1 004 663 A1 | 5/2000 |
| EP | 1 038 970 A2 | 9/2000 |
| EP | 1 197 555 A1 | 4/2002 |
| WO | WO 95/10613 | 4/1995 |
| WO | WO 97/01637 | 1/1997 |
| WO | WO 98/18937 | 5/1998 |
| WO | WO 00/37647 | 6/2000 |
| WO | WO 01/05959 | 1/2001 |
| WO | WO 02/12481 | 2/2002 |
| WO | WO 03/008607 | 1/2003 |

OTHER PUBLICATIONS

Kraemer, Reinhard, "Minireview; Genetic and physiological approaches for the production of amino acids", Journal of Biotechnology, 1996, vol. 45, pp. 1-21.
European Search Report by European Patent Office issued on Sep. 23, 2004.
Chye M. et al., "Cloning of the *aroP* Gene and Identification of Its Product in *Escherichia coli* K-12", Journal of Bacteriology, 1986, vol. 167, No. 2, pp. 749-753.
Sarsero J. P. et al., "A New Family of Integral Membrane Proteins Involved in Transport of Aromatic Amino Acids in *Escherichia coli*", Journal of Bacteriology, 1991, vol. 173, No. 10, pp. 3231-3234.
Heatwole V. M. et al., "The Tryptophan-Specific Permease Gene, *mtr*, Is Differentially Regulated by the Tryptophan and Tyrosine Repressors in *Escherichia coli* K-12", Journal of Bacteriology, 1991, vol. 173, No. 11, pp. 3601-3604.

*Primary Examiner*—James Ketter
(74) *Attorney, Agent, or Firm*—Shelly Guest Cermak Cermak Kenealy & Vaidya LLP

(57) ABSTRACT

A target substance is produced by culturing a bacterium which has the ability to produce the target substance in a medium to cause accumulation of said target substance in the medium and collecting the target substance from the medium, wherein the bacterium is modified so that a system for uptake of a byproduct of the target substance or a substrate for a biosynthesis system of the target substance into the bacterial cell.

7 Claims, No Drawings

US 7,335,496 B2

METHOD FOR PRODUCING TARGET SUBSTANCE

BACKGROUND OF THE INVENTION

1. Field of the Invention

The present invention relates to a method for producing a target substance by using a bacterium. More specifically, the present invention relates to a method for improving production of a target substance such as an L-amino acid, nucleic acid, antibiotic, vitamin, growth factor or physiologically active substance by using a bacterium.

2. Description of the Related Art

The production of target substances such as L-amino acids by fermentation using microorganisms includes the following methods: a method of using a wild-type microorganism (wild-type strain), a method of using an auxotrophic strain derived from a wild-type strain, a method of using a metabolically-regulated mutant derived from a wild-type strain as one of various drug resistant mutants, a method of using a strain having characteristics of both of an auxotrophic strain and a metabolically-regulated mutant and so forth.

In recent years, recombinant DNA techniques have been used for the production of target substances by fermentation. For example, the ability of microorganisms to produce L-amino acids can be improved by enhancing a gene encoding an L-amino acid biosynthesis enzyme (U.S. Pat. Nos. 5,168,056 and 5,776,736), or by enhancing inflow of a carbon source into an L-amino acid biosynthesis system (U.S. Pat. No. 5,906,925).

Methods for improving the production of target substances in a microorganism include methods of modifying the uptake or excretion system of a substance. Examples of a method for modifying an uptake system include a method for improving a target substance-producing ability by deleting or degrading a system for uptake of the target substance into a cell. Specifically, a method of deleting the gluABCD operon or a part thereof to delete or degrade an L-glutamic acid uptake system (EP 1 038 970 A1), a method of attenuating uptake of purine nucleosides into a cell to enhance the purine nucleoside-producing ability (EP 1 004 663 A1), and so forth are known.

Methods for modifying an excretion system of a microorganism include a method of enhancing an excretion system for a target substance and a method of deleting or attenuating an excretion system for an intermediate or substrate of a biosynthesis system of a target substance. As the method of enhancing an excretion system of a target substance, for example, a method for producing L-lysine by using a *Corynebacterium* bacterium strain in which expression of an L-lysine excretion gene (lysE) is enhanced (WO97/23597) has been disclosed. As for the latter method, a method is known for producing L-glutamic acid as a target substance, in which excretion of α-ketoglutaric acid, an intermediate of the target substance, is reduced by mutating or disrupting the α-ketoglutarate permease gene (WO01/005959).

Furthermore, it has been suggested that the gene encoding the ATP binding cassette superfamily (ABC transporter) involved in permeation of substances through a cell membrane is used for the breeding of microorganisms in which amino acid transport through the cell membrane is modified (WO00/37647).

Furthermore, it has been suggested that the gene encoding sucrose PTS enzyme II, a protein involved in the uptake of sucrose into a cell, is used in a coryneform bacterium for breeding of a strain exhibiting improved productivity of an amino acid, nucleic acid etc. (EP 1 197 555 A). Furthermore, a technique for improving L-amino acid productivity of a bacterium belonging to the genus *Escherichia* using a sucrose PTS gene group or a sucrose non-PTS gene group (U.S. Patent Application No. 2001/0049126) is also known.

A technique for reducing production of a byproduct of a target substance by deleting or attenuating the biosynthesis system of the byproduct (for example, "Amino Acid Fermentation" Gakkai Shuppan Center, p. 4, 1986) is known. However, in this method, when a microorganism is cultured, the aforementioned byproduct needs to be added to a medium in an amount necessary for growth.

Mtr (Heatwole, V. M. et al., J. Bacteriol., American Society for Microbiology, 173, pp. 108-115, January 1991) and TnaB (Sarsero, J. P. et al., J. Bacteriol., American Society for Microbiology, 173(10), pp. 3231-3234, May 1991) are known as L-tryptophan-specific uptake systems, and AroP (Mee-Len, C. et al., J. Bacteriol., American Society for Microbiology, 167(2), pp. 749-753, August 1986) is known as an uptake system common to aromatic amino acids. However, it has not been previously described to improve productivity of a target substance by enhancing an uptake system for a byproduct of the target substance.

SUMMARY OF THE INVENTION

An object of the present invention is to provide a method for producing a target substance such as an L-amino acid, antibiotic, vitamin, growth factor or physiologically active substance using a bacterium, wherein production of a byproduct is reduced, and preferably production of the target substance is improved.

It is a further object of the present invention to provide a method for producing a target substance comprising culturing a bacterium which has an ability to produce the target substance in a medium, and collecting the target substance from the medium, wherein said bacterium is modified so that a system for cell uptake of either a byproduct of the target substance or a substrate for a biosynthesis system of the target substance is enhanced.

It is a further object of the present invention to provide the method described above, wherein said byproduct is selected from the group consisting of an intermediate in a biosynthetic pathway of said target substance, a substrate in a biosynthetic pathway of said target substance, and a product of another biosynthesis system branching off from said pathway.

It is a further object of the present invention to provide the method described above, wherein the bacterium belongs to the genus *Escherichia*.

It is a further object of the present invention to provide the method described above, wherein said target substance is L-phenylalanine and said byproduct is L-tryptophan.

It is a further object of the present invention to provide the method described above, wherein said system for uptake of a byproduct is selected from the group consisting of Mtr and TnaB.

It is a further object of the present invention to provide the method described above, wherein an activity of said system is increased by a method selected from the group consisting of increasing a copy number of an mtr gene or tnaB gene, and modifying an expression regulatory sequence of an mtr gene or tnaB.

It is a further object of the present invention to provide a bacterium belonging to the genus *Escherichia*, which has an ability to produce a target substance and has a modification selected from the group consisting of enhancement of a system for cell uptake of a byproduct of the target substance; and enhancement of a system for cell uptake of a substrate for a biosynthesis system of the target substance.

It is a further object of the present invention to provide the bacterium described above, wherein said target substance is L-phenylalanine, and said byproduct is L-tryptophan, and said system for cell uptake is selected from the group consisting of Mtr and TnaB.

It is a further object of the present invention to provide the bacterium described above, wherein an activity of Mtr or TnaB is increased by a method selected from the group consisting of increasing the copy number of an mtr gene or tnaB gene; and modifying an expression regulatory sequence of an mtr gene or tnaB gene.

It is a further object of the present invention to provide the bacterium or the method as described above, wherein said mtr gene comprises a DNA sequence selected from the group consisting of the DNA sequence which encodes a protein sequence shown in SEQ ID No. 2, the DNA sequence shown in SEQ ID No. 1, and the DNA sequence which encodes a protein sequence shown in SEQ ID No. 2, and which has been modified to have substitutions, deletions, insertions, or additions one or several amino acid residues at one or several sites and has at least 70% homology to the sequence shown in SEQ ID No. 2, wherein said mtr gene encodes a protein which has the activity of a Mtr protein.

It is a further object of the present invention to provide the method or bacterium as described above, wherein said tnaB gene comprises a DNA sequence selected from the group consisting of the DNA sequence which encodes a protein sequence shown in SEQ ID No. 4, the DNA sequence shown in SEQ ID No. 3, and the DNA sequence which encodes a protein sequence shown in SEQ ID No. 4, and which has been modified to have substitutions, deletions, insertions, or additions one or several amino acid residues at one or several sites and has at least 70% homology to the sequence shown in SEQ ID No. 4, wherein said tnaB gene encodes a protein which has the activity of a TnaB protein.

According to the present invention, when a target substance such as an L-amino acid is produced using a bacterium, production of a byproduct can be reduced. According to a preferred embodiment of the present invention, production of the target substance can be improved.

Furthermore, when a bacterium is cultured, no substance required for growth needs to be added to a medium. Furthermore, since the amount of a byproduct in the medium can be reduced, purification of the target substance from the medium becomes easy.

DETAILED DESCRIPTION OF THE PREFERRED EMBODIMENTS

The inventors of the present invention assiduously studied in order to achieve the foregoing object. As a result, it was found that when a bacterium was modified so that a system for cell uptake of a byproduct of a target substance is enhanced, the production of that byproduct was reduced, and thus accomplished the present invention.

The bacterium of the present invention produces a target substance and is modified so that a system for cell uptake of either a byproduct of the target substance or a substrate for a biosynthesis system of the target substance is enhanced. The bacterium of the present invention is not particularly limited so long as it produces a target substance and has a system for cell uptake of either a byproduct of the target substance or a substrate for a biosynthesis system of the target substance. Furthermore, so long as the above requirements are satisfied, the present invention can also be applied to bacteria which have not been previously used in industry. The bacterium of the present invention may have an inherent ability to produce a target substance, or the ability may be imparted by breeding using a mutation method, a recombinant DNA technique or the like.

Specific examples of the bacterium include bacteria belonging to the genus *Escherichia*, such as *Escherichia coli*, coryneform bacteria such as *Brevibacterium lactofermentum*, bacteria belonging to the genus *Bacillus* such as *Bacillus subtilis*, bacteria belonging to the genus *Serratia* such as *Serratia marcescens*, and so forth. However, the bacterium of the present invention is not limited to these examples.

The expression "produce a target substance" means that, when a bacterium of the present invention is cultured in a medium, the bacterium exhibits an ability to produce the target substance in such an amount that the target substance can be collected from the bacterial cells or from the medium. Preferably, it means that the bacterium exhibits an ability to produce the target substance in an amount that is larger than is produced by a wild-type or unmodified strain of the bacterium.

The target substance produced by the present invention is not particularly limited so long as it is a substance that can be produced by a bacterium. Examples thereof include various L-amino acids such as L-phenylalanine, L-threonine, L-lysine, L-glutamic acid, L-leucine, L-isoleucine and L-valine. In addition, the target substance may be any substance that can be biosynthesized by bacteria, including nucleic acids such as guanylic acid and inosinic acid, vitamins, antibiotics, growth factors, physiologically active substances etc., so long as a uptake system exists for an intermediate or substrate in the biosynthesis thereof. Furthermore, the present invention can be used to produce a substance which is not currently produced by using a bacterium so long as an cell uptake system for either a byproduct of the target substance or a substrate for a biosynthesis system of the target substance exists.

Examples of a L-phenylalanine-producing bacteria include *Escherichia coli* AJ12741 (FERM P-13000, see Japanese Patent No. 3225597) and AJ12604 (FERM BP-3579, see European Patent Application Laid-open No. 488,424), *Brevibacterium lactofermentum* AJ12637 (FERM BP-4160, see French Patent Application Laid-open No. 2,686,898) and so forth. In addition, examples of bacteria producing L-threonine as a target substance include *Escherichia coli* VKPM B-3996 (RIA 1867, see U.S. Pat. No. 5,175,107), *Corynebacterium acetoacidophilum* AJ12318 (FERM BP-1172, see U.S. Pat. No. 5,188,949) and so forth. Examples of L-lysine-producing bacteria include *Escherichia coli* AJ11442 (NRRL B-12185, FERM BP-1543, see U.S. Pat. No. 4,346,170), *Brevibacterium lactofermentum* AJ3990 (ATCC31269, see U.S. Pat. No. 4,066,501) and so forth. Examples of L-glutamic acid-producing bacteria include *Escherichia coli* AJ12624 (FERM BP-3853, see French Patent Application Laid-open No. 2,680,178), *Escherichia coli* AJ13199 (FERM P-15573, see Japanese Patent Laid-open No. 7-203980), *Brevibacterium lactofermentum* AJ12475 (FERM BP-2922, see U.S. Pat. No. 5,272,067) and so forth. Examples of L-leucine-producing bacteria include *Escherichia coli* AJ11478 (FERM P-5274, see Japanese Patent Publication (Kokoku) No. 62-34397), *Brevibacterium lactofermentum* AJ3718 (FERM P-2516, see U.S. Pat. No. 3,970,519) and so forth. Examples of L-isoleucineproducing bacteria include *Escherichia coli* KX141 (VKPM B-4781, see European Patent Application Laid-open No. 519,113), *Brevibacterium flavum* AJ12149 (FERM BP-759, see U.S. Pat. No. 4,656,135) and so forth. Examples of L-valine-producing bacteria include *Escherichia coli* VL1970 (VKPM B-4411, see European Patent Application Laid-open No. 519,113), *Brevibacterium lactofermentum* AJ12341 (FERM BP-1763, see U.S. Pat. No. 5,188,948) and so forth.

In the present invention, a "byproduct" of a target substance means a substance other than the target substance produced as a byproduct during the production of the target substance.

Furthermore, in the present invention, if the bacterium includes an uptake system for the byproduct or substrate and it is unmodified as taught by the present invention, the "byproduct" and "substrate for a biosynthesis system of the target substance" are secreted, and therefore, accumulate in a medium when the bacterium is cultured.

The terms "target substance" and "byproduct" have relative concepts, and whether a substance is a target substance or a byproduct depends on the object to be produced. For example, when L-phenylalanine is to be produced, L-phenylalanine is a target substance, and L-tryptophan produced during the production of L-phenylalanine is a byproduct. When L-tryptophan is to be produced, L-tryptophan is a target substance, and L-phenylalanine produced during the production of L-tryptophan is a byproduct.

Specific examples of a byproduct of the present invention include an intermediate in a biosynthetic pathway of a target substance, a product of another biosynthesis system which branches off from the pathway, and so forth. The intermediate or substrate is not limited to an intermediate or substrate in a biosynthesis system unique to the target substance, such as a precursor, and it may be an intermediate or substrate in a biosynthesis system or metabolic system of another substance, for example, an intermediate or substrate of the glycolytic system when the target substance is an L-amino acid. Hereinafter, the aforementioned "byproduct" or "substrate" may be genetically referred to as a byproduct, and descriptions regarding a byproduct are similarly applicable to a substrate.

In the present invention, the "system for cell uptake," or a system for uptake into a cell, refers to a protein involved in the uptake into a cell of the aforementioned byproduct, which had been secreted to the outside of a cell. The uptake system may consist of a single protein or two or more proteins. Furthermore, two or more kinds of uptake systems may exist for a single kind of byproduct.

The expression "modified so that an uptake system is enhanced" means that the bacterium is modified so that the uptake amount or the uptake rate of the aforementioned byproduct is increased compared with those of unmodified strains, for example, wild-type bacteria. For example, if the activity of a protein constituting the uptake system is increased as compared to a wild-type or unmodified strain by increasing the amount or specific activity of the protein, the aforementioned uptake system is enhanced. The activity of a protein constituting the uptake system can be determined by the method described in Sarsero, J. P. et al., J. Bacteriol., 177(2), 297-306, 1995, for example, when the protein is Mtr, TnaB, TyrP, PheP or AroP. Activities of NupC and NupG derived from *Escherichia coli* can be determined by the method described in J. Bacteriol., 183(16), 4900-4, August 2001. Activity of GluABCD derived from *Corynebacterium glutamicum* can be determined by the method described in J. Bacteriol., 177(5), 1152-8, March 1995. Activity of BrnQ derived from *Corynebacterium glutamicum* can be determined by the method described in Arch. Microbiol., 169(4), 303-12, April 1998. Activities of LivFGHJKM and LivK derived from *Escherichia coli* can be determined by the methods described in J. Biol. Chem., 15, 265(20), 11436-43, July 1990; J. Bacteriol., 116, 1258-66, 1973; and J. Bacteriol., 174(1), 108-15, January 1992. Activity of LysP derived from *Escherichia coli* can be determined by the method described in J. Bacteriol., 174 (10), 3242-9, May 1992. Activity of ArtPIQMJ derived from *Escherichia coli* can be determined by the method described in Mol. Microbiol., 17(4), 675-86, August 1995.

As for *Escherichia coli* bacteria, for example, an example of the wild-type bacterium to be compared is the *Escherichia coli* MG1655 strain.

Examples of combination of target substance, byproduct or substrate in their biosynthesis system and uptake system thereof are shown in Table 1.

TABLE 1

| bacteria | target substance | byproduct | uptake system gene |
|---|---|---|---|
| *E. coli* | L-phenylalanine, L-tyrosine etc. | L-tryptophan | mtr, tnaB |
| *E. coli* | L-phenylalanine, L-tryptophan etc. | L-tyrosine | tyrP |
| *E. coli* | L-tyrosine, L-tryptophan etc. | L-phenylalanine | pheP |
| *E. coli* | substances other than aromatic amino acids | aromatic amino acids | aroP, pheP, tyrP |
| *E. coli* | substances other than branched amino acid | branched amino acids | brnQ, livFGHJKM |
| *E. coli* | substances other than L-lysine | L-lysine | lysP |
| *E. coli* | substance other than L-threonine and L-serine | L-threonine, L-serine | tdcC, sdaC |
| *E. coli* | substance other than L-arginine | L-arginine | artIJMPQ |
| *E. coli* | substance other than L-leucine, e.g., L-isoleucine, L-valine etc. | L-Leucine | livK |
| *E. coli* | substance other than uracil | uracil | uraA |

TABLE 1-continued

| bacteria | target substance | byproduct | uptake system gene |
|---|---|---|---|
| E. coli | substances other than nucleosides | nucleosides | nupC, nupG |
| coryneform bacteria | substances other than L-glutamic acid, e.g., L-glutamine etc. | L-glutamic acid | gluABCD |
| coryneform bacteria | substances other than L-lysine | L-lysine | lysI |

A particularly preferred example of the target substance of the present invention is L-phenylalanine. Furthermore, an example of the byproduct thereof is L-tryptophan.

A preferred example of the bacterium belonging to the genus Escherichia producing L-phenylalanine is the Escherichia coli AJ12741 strain. This strain was constructed by introducing a plasmid pMGAL1 into the Escherichia coli K-12 W3110 strain which is deficient in the tyrR and tyrA genes (W3110(tyrR,tyrA)/pMGAL1, Japanese Patent No. 3225597). The plasmid pMGAL1 contains genes encoding 3-deoxy-D-arabino-heptulonate-7-phosphate synthase (DS) for which feedback inhibition is desensitized, chorismate mutase/prephenate dehydratase (CM-PD) for which feedback inhibition is desensitized, and shikimate kinase. This strain was deposited at National Institute of Bioscience and Human-Technology, Agency of Industrial Science and Technology, Ministry of International Trade and Industry (currently the independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Jun. 11, 1992 and received an accession number of FERM P-13000. Then, it was converted to an international deposit under the provisions of the Budapest Treaty on Sep. 14, 1994, and received an accession number of FERM BP-4796.

Furthermore, the aforementioned Escherichia coli AJ12604 strain is also a preferred example of an L-phenylalanine-producing bacterium. This strain was constructed by introducing plasmids pBR-aroG4, which contains a gene encoding DS for which feedback inhibition is desensitized, and pACMAB, which contains a gene encoding CM-PD for which feedback inhibition is desensitized, into the Escherichia coli K-12 W3110 strain which is deficient in the tyrA gene (European Patent Application Laid-open No. 488,424). This strain was deposited at National Institute of Bioscience and Human-Technology, Agency of Industrial Science and Technology, Ministry of International Trade and Industry (currently the independent administrative agency, National Institute of Advanced Industrial Science and Technology, International Patent Organism Depositary) on Jan. 28, 1991, and received an accession number of FERM P-11975. Then, it was converted into an international deposit under the provisions of the Budapest Treaty on Sep. 26, 1991, and received an accession number of FERM BP-3579.

Examples of the L-tryptophan uptake system include Mtr and TnaB. The gene encoding Mtr (mtr) and the gene encoding TnaB (tnaB) of Escherichia coli have already been reported (Heatwole, V. M., J. Bacteriol., 173, 108-115, 1991; Sarsero, J. P., J. Bacteriol., 173(10), 3231-3234, 1991). These genes can be obtained by, for example, PCR (polymerase chain reaction) using a chromosomal DNA of Escherichia coli as a template (see White, T. J. et al., Trends Genet. 5, 185, 1989). Examples of primers for amplification of mtr include oligonucleotides having the nucleotide sequences of SEQ ID NOS: 5 and 6. Examples of primers for amplification of tnaB include oligonucleotides having the nucleotide sequences of SEQ ID NOS: 7 and 8. Examples of sources of the aforementioned chromosomal DNA include a wild-type strain of Escherichia coli, for example, the W3110 strain (ATCC39936). For tnaB, since IS (insertion sequence) is inserted into the W3110 strain tnaB, and TnaB encoded by this gene does not have activity (Kamath, A. V. et al., J. Bacteriol., 176(5), 1546-1547, 1994), other bacterial strains containing functional TnaB are used. Examples of sources for obtaining tnaB include the Escherichia coli MG1655 strain (ATCC700926), JM109 strain, and so forth. The W3110 strain and the MG1655 strain can be obtained from the American Type Culture Collection (10801 University Boulevard, Manassas, Va., 20110-2209, U.S.A.). The JM109 strain is commercially available from Takara Shuzo Co., Ltd., etc.

The nucleotide sequence of mtr and the amino acid sequence of Mtr encoded by this gene are shown in SEQ ID NOS: 1 and 2. The nucleotide sequence of tnaB and the amino acid sequence of TnaB encoded by this gene are shown in SEQ ID NOS: 3 and 4.

mtr or tnaB used in the present invention may encode Mtr or TnaB, respectively, including substitution, deletion, insertion or addition of one or several amino acid residues at one or several sites so long as the activity of the encoded protein, Mtr or TnaB, is not diminished. The number of "several" amino acid residues used herein varies depending on positions of amino acid residues in the three-dimensional structure of the protein and types of the amino acid residues. However, it is specifically 2 to 30, preferably 2 to 20, more preferably 2 to 10.

A DNA encoding a protein substantially identical to the aforementioned Mtr or TnaB can be obtained by modifying the nucleotide sequence of mtr or tnaB. For example, site-directed mutagenesis can be employed so that substitution, deletion, insertion, addition or inversion of an amino acid residue or residues occur at a specific site. Furthermore, a DNA modified as described above can also be obtained by a conventionally-known mutagenesis treatment. Examples of the mutagenesis treatment include a method of treating a DNA in vitro with hydroxylamine or the like and a method of treating a microorganism, for example, a bacterium belonging to the genus Escherichia, containing a DNA with ultraviolet ray irradiation or a mutagenesis agent used in a conventional mutagenesis treatment such as N-methyl-N'-nitro-N-nitrosoguanidine (NTG), EMS and so forth.

A DNA encoding a protein substantially identical to Mtr or TnaB can be obtained by expressing a DNA including any of the aforementioned mutations in a suitable cell, and examining the activity of the expression product. Furthermore, for example, a DNA which is hybridizable with a probe having the nucleotide sequence of nucleotide numbers 181 to 1425 of SEQ ID NO: 1 (coding region of mtr) or the nucleotide sequence of nucleotide numbers 91 to 1338 of SEQ ID NO: 3 (coding region of tnaB) or a part of these sequences under stringent conditions and encodes a protein having the same activity as Mtr or TnaB can be obtained from a DNA encoding Mtr or TnaB having a mutation or a cell containing such a DNA. The "stringent conditions" referred to herein are defined as conditions under which a so-called specific hybrid is formed, and a non-specific hybrid is not formed. It is difficult to clearly express this condition by using any numerical value. However, the stringent conditions includes, for example, conditions under which DNAs having a high homology, for example, DNAs having a homology of 70% or more, preferably 80% or more, more preferably 90% or more, most preferably 95% or more, hybridize with each other, but DNAs having a homology lower than the above do not hybridize with each other. Alternatively, the stringent conditions are exemplified by conditions whereby DNAs hybridize with each other at a salt concentration corresponding to typical conditions of washing for Southern hybridization, i.e., 1×SSC, 0.1% SDS, preferably 0.1×SSC, 0.1% SDS, at 60° C.

A partial sequence of the nucleotide sequence of SEQ ID NO: 1 or 3 can also be used as the probe. Such a probe can be produced by PCR using oligonucleotides prepared based on the nucleotide sequence of SEQ ID NO: 1 or 3 as primers and a DNA fragment including the nucleotide sequence of SEQ ID NO: 1 or 3 as a template. When a DNA fragment having a length of about 300 bp is used as the probe, the washing conditions for hybridization may be 2×SSC, 0.1% SDS at 50° C.

Specific examples of a DNA encoding a protein substantially identical to Mtr include a DNA encoding a protein having a homology of preferably 70% or more, more preferably 80% or more, further preferably 90% or more, most preferably 95% or more, with respect to the amino acid sequence of SEQ ID NO: 2 and having the activity comparable to that of Mtr. Furthermore, specific examples of a DNA encoding substantially the same protein as TnaB include a DNA encoding a protein having homology of preferably 70% or more, more preferably 80% or more, further preferably 90% or more, most preferably 95% or more, with respect to the amino acid sequence of SEQ ID NO: 4 and having the activity in a degree comparable to that of TnaB.

A homologue of mtr or tnaB of other bacteria can be obtained in the same manner as that used for the aforementioned mtr or tnaB of *Escherichia coli*. Furthermore, genes encoding uptake systems other than mtr or tnaB can also be obtained by PCR from a chromosomal DNA of bacteria using well-known and usual methods for obtaining genes.

A chromosomal DNA can be prepared from a bacterium as a DNA donor by, for example, the method of Saito and Miura (see Saito H. and Miura K., Biochem. Biophys. Acta, 72, 619, 1963; Seibutsu Kogaku Jikkensho (Text for Bioengineering Experiments), Edited by the Society for Bioscience and Bioengineering, Japan, 97-98, Baifukan, 1992) or the like.

If a recombinant DNA is prepared by ligating the obtained gene with a vector DNA autonomously replicable in a cell of *Escherichia coli* and/or an objective bacterium and introduced into *Escherichia coli*, subsequent operations become easier. Examples of vectors autonomously replicable in *Escherichia coli* cells include pSTV29, pUC 19, pUC18, pHSG299, pHSG399, pHSG398, RSF1010, pBR322, pACYC184, pMW219 and so forth.

To prepare a recombinant DNA by ligating the obtained gene to a vector that functions in an objective bacterium, the vector can be digested with restriction enzymes providing digested ends matching the ends of the aforementioned gene, and the aforementioned gene and the vector can be ligated by using a ligase such as T4 DNA ligase.

An uptake system for a byproduct of a target substance can be enhanced by enhancing the expression of a gene encoding a protein which is a part of the uptake system. The expression amount of the gene is increased by increasing the copy number of the gene. For example, the aforementioned gene fragment can be ligated to a vector that functions in a bacterium, preferably a multi-copy type vector, to prepare a recombinant DNA, which is then used to transform the host producing a target substance. Furthermore, the aforementioned recombinant DNA may be introduced into a wild-type bacterium to obtain a transformant strain, and then a target substance-producing ability may be imparted to the transformant strain.

Any known transformation methods that have hitherto been reported can be employed for introduction of a recombinant DNA into a bacterium. For instance, a method of treating recipient bacterial cells with calcium chloride so as to increase permeability of the cells for DNA in known and has been reported for the *Escherichia coli* K-12, (Mandel, M. and Higa, A., J. Mol. Biol., 53, 159, 1970), and a method of preparing competent cells from cells which are at the growth phase followed by introducing DNA into them is also known and has been reported for *Bacillus subtilis* (Duncan, C. H., Wilson, G. A. and Young, F. E., Gene, 1, 153, 1977). Furthermore, a method of making DNA-recipient cells into protoplasts or spheroplasts, which can easily take up a recombinant DNA, followed by introducing the recombinant DNA into the DNA-acceptor cells, which is known for *Bacillus subtilis*, actinomycetes and yeasts is also known (Chang, S. and Choen, S. N., Molec. Gen. Genet., 168, 111, 1979; Bibb, M. J., Ward, J. M. and Hopwood, O. A., Nature, 274, 398, 1978; Hinnen, A., Hicks, J. B. and Fink, G R., Proc. Natl. Acad. Sci., USA, 75, 1929, 1978). Transformation of microorganisms can also be performed by the electric pulse method (Japanese Patent Laid-open No. 2-207791).

The copy number of a gene can also be increased by allowing multiple copies of the gene to exist on a chromosomal DNA of the bacterium. In order to introduce multiple copies of the gene into the chromosomal DNA, homologous recombination can be performed using a sequence that is present on the chromosomal DNA in a multiple copy number as a target. As the sequence present on a chromosomal DNA in a multiple copy number, a repetitive DNA or inverted repeat present at the end of a transposable element can be used. Alternatively, as disclosed in Japanese Patent Laid-open No. 2-109985, multiple copies of the desired gene can be introduced into a chromosomal DNA by incorporating them into a transposon and transferring it.

Besides by the aforementioned gene amplification, an uptake system can also be enhanced by replacing an expression regulatory sequence such as a promoter of the gene encoding the uptake system on a chromosomal DNA or a plasmid with a stronger one. For example, lac promoter, trp promoter, trc promoter and so forth are known as strong promoters. Furthermore, as disclosed in International Patent Publication WO00/18935, a promoter can also be modified to a stronger one by introducing substitution of several nucleotides into the promoter region of the gene. The aforementioned substitution or modification of a promoter enhances expression of the gene encoding the uptake system, and thus the uptake system is enhanced. Modification of an expression regulatory sequence can be combined with increase of the copy number of the gene.

Substitution of the expression regulatory sequence can be performed, for example, in the same manner as in gene substitution using a temperature sensitive plasmid. Examples of vectors having a temperature-sensitive replication origin of *Escherichia coli* include, for example, plasmid pMAN997 described in International Publication WO99/03988, and so forth. Furthermore, substitution of the expression regulatory sequence can also be performed by a method using Red recombinase of λ phage (Datsenko, K. A., PNAS, 97(12), 6640-6645, 2000).

Furthermore, as shown in the example section, substitution of the expression regulatory sequence can also be performed by a method with combination of a system utilizing Red recombinase of λ phage and P1 transduction as follows. First, the expression regulatory sequence which is obtained by PCR is introduced into a strain derived from *E. coli* W3110 strain used for a donor by a method using Red recombinase of λ phage. Then, the expression regulatory sequence is transduced into an acceptor strain from the donor strain by P1 transduction. The donor strain is not limited so long as it is a derivative of the W3110 strain and it has a substituted expression regulatory sequence.

Furthermore, in the bacterium of the present invention, a system for uptake of a target substance into a cell may be deleted or degraded. Furthermore, an excretion system of the target substance may be enhanced.

The target substance can be efficiently produced by culturing the bacterium of the present invention obtained as described above in a medium to cause accumulation of the target substance in the medium and collecting the target substance from the medium.

The target substance of the present invention can be produced as the same way as it usually is produced, except that the bacterium of the present invention is used. The culture conditions can be suitably selected depending on the bacterium.

For example, the medium may be a typical medium containing a carbon source, nitrogen source, inorganic ions and other organic components as required. Saccharides such as glucose, lactose, galactose, fructose, arabinose, maltose, xylose, trehalose, ribose and hydrolysate of starch, alcohols such as glycerol, mannitol and sorbitol and organic acids such as gluconic acid, fumaric acid, citric acid and succinic acid can be used as the carbon source. Inorganic ammonium salts such as ammonium sulfate, ammonium chloride and ammonium phosphate, organic nitrogen such as soybean hydrolysate, ammonia gas, aqueous ammonia and so forth can be used as the nitrogen source. As for organic trace nutrients, it is preferable to add required substances, for example, vitamins such as vitamin B1, nucleic acids such as adenine and RNA, yeast extract and so forth in suitable amounts. In addition to these substances, small amounts of calcium phosphate, magnesium sulfate, iron ion, manganese ion and so forth are added, as required. If the bacterium of the present invention is deficient in the tyrA gene, L-tyrosine required for growth is added to the medium.

In the case of *Escherichia coli*, for example, the culture is preferably performed under aerobic conditions for about 16 to 72 hours. The culture temperature is controlled to be 30 to 45° C., and pH is controlled to be 5 to 8 during the culture. Inorganic or organic, acidic or alkaline substances as well as ammonia gas and so forth can be used to adjust pH.

Collection of the target substance from the medium can be performed using a combination of well-known methods. Such methods typically use ion exchange resins, precipitation and others depending on the target substance.

EXAMPLES

The present invention will be explained more specifically, with reference to the following non-limiting examples.

Example 1

<1> Construction of mtr Gene-carrying Plasmid and tnaB Gene-carrying Plasmid

Construction of mtr Gene-carrying Plasmid

PCR was performed using a chromosomal DNA of the *Escherichia coli* W3110 strain as a template and oligonucleotides having the nucleotide sequences of SEQ ID NOS: 5 and 6 as primers. PCR was performed using LATaq (Takara Shuzo) with a cycle of 94° C. for 2 minutes (1 cycle), followed by 30 cycles of 94° C. for 30 seconds, 55° C. for 30 seconds and 72° C. for 1 minute 30 seconds. An amplified fragment of about 1.5 kb, including a promoter and ORF of mtr, was obtained.

The above-amplified fragment was purified using MicroSpins™ S400HR Columns (Amarsham Pharmacia Biotech Inc.), then digested with SacI and KpnI and ligated to pSTV28 and pSTV29 (Takara Shuzo) which had been similarly digested with SacI and KpnI. *Escherichia coli* JM109 Competent Cells (Takara Shuzo) were transformed with this reaction mixture. The transformants were cultured on an LB plate containing chloramphenicol, IPTG and X-Gal. White colonies were selected. mtr-carrying plasmids pSTV28mtr and pSTV29mtr were obtained from the selected transformants.

In pSTV28mtr, the mtr gene was inserted in the same direction as the lac promoter. On the other hand, in pSTV29mtr, the mtr gene was inserted in the opposite direction relative to the lac promoter.

(2) Construction of tnaB Gene-carrying Plasmid

PCR was performed using a chromosomal DNA of the *Escherichia coli* MG1655 strain as a template and oligonucleotides having the nucleotide sequences of SEQ ID NOS: 7 and 8 as primers. PCR was performed using LATaq (Takara Shuzo) with a cycle of 94° C. for 2 minutes (1 cycle), followed by 30 cycles of 94° C. for 30 seconds, 55° C. for 30 seconds and 72° C. for 1 minute 30 seconds. An amplified fragment of about 1.5 kb including ORF of tnaB was obtained. tnaB formed an operon with tnaA, and no promoter existed immediately upstream from tnaB.

The above amplified fragment was purified using MicroSpins™ S400HR Columns (Amarsham Pharmacia Biotech Inc.), then digested with SalI and PstI and ligated to pSTV28 and pSTV29 (Takara Shuzo) which had been similarly digested with SalI and PstI. *Escherichia coli* JM109 Competent Cells (Takara Shuzo) were transformed with this reaction mixture. The transformants were cultured on an LB plate containing chloramphenicol, IPTG and X-Gal, and white colonies were selected. tnaB-carrying plasmids pSTV28tnaB and pSTV29tnaB were obtained from the selected transformants.

In pSTV28tnaB, the tnaB gene was inserted in the same direction as the lac promoter. On the other hand, in pSTV29tnaB, the tnaB gene was inserted in the opposite direction relative to the lac promoter.

<2> Construction of mtr and tnaB-enhanced Strains and Production of L-phenylalanine The aforementioned plasmids pSTV28mtr, pSTV29mtr, pSTV28tnaB and pSTV29tnaB were introduced into an L-phenylalanine-producing bacterium of Escherichia coli, the AJ12741 strain (see Japanese Patent No. 3225597, hereinafter also referred to as "R/GAL strain") in a conventional manner to obtain R/GAL/pSTV28mtr, R/GAL/pSTV29mtr, R/GAL/pSTV28tnaB and R/GAL/pSTV29tnaB. The L-phenylalanine-producing abilities of these transformants and the R/GAL strain were then evaluated.

20 ml of a medium having the following composition was introduced into a Sakaguchi flask (500 ml), and each bacterial strain was inoculated and cultured at 37° C. until all the glucose was consumed. The amounts of L-phenylalanine (L-Phe) and L-tryptophan (L-Trp) which had accumulated in the medium after the culture were measured. The results are shown in Table 2.

| Medium composition (pH 7.0): | |
|---|---|
| Glucose | 40 g/L |
| Magnesium sulfate heptahydrate | 1 g/L |
| Ammonium sulfate | 16 g/L |
| Potassium dihydrogen phosphate | 1 g/L |
| Yeast extract | 2 g/L |
| Iron(I) sulfate heptahydrate | 10 mg/L |
| Manganese sulfate tetra or pentahydrate | 8 mg/L |
| L-Tyrosine | 125 mg/L |
| Ampicillin | 50 mg/L |
| Chloramphenicol (not added for the R/GAL strain) | 50 mg/L |
| Calcium carbonate | 30 g/L |

TABLE 2

| Bacterial strain | L-Phe (g/L) | L-Trp (mg/L) |
|---|---|---|
| R/GAL | 6.8 | 60 |
| R/GAL/pSTV28mtr | 6.6 | <1.5 |
| R/GAL/pSTV29mtr | 6.7 | <1.5 |
| R/GAL/pSTV28tnaB | 6.6 | <1.5 |
| R/GAL/pSTV29tnaB | 6.7 | <1.5 |

As shown in Table 2, the R/GAL strain produced L-tryptophan as a byproduct. However, the mtr-enhanced strains and tnaB-enhanced strains did not produce L-tryptophan as a byproduct, and were able to cause accumulation of L-phenylalanine in an amount comparable to that obtained with the R/GAL strain.

Example 2

<1> Construction of mtr Gene Promoter-enhanced Strain and tnaB Gene Promoter-enhanced Strain By using a method which combines a system utilizing Red recombinase of λ phage (Datsenko, K. A., PNAS, 97(12), 6640-6645, 2000) and P1 transduction, the $P_L$ promoter of λ phage was inserted into the coding regions of the mtr gene and the tnaB gene on the chromosome of Escherichia coli to construct an mtr gene promoter-enhanced strain and a tnaB gene promoter-enhanced strain.

First, a λ phage-derived attR sequence (1), a Tn9-derived cat gene (2), a T7 phage-derived Pa2 promoter sequence (3), a pBR322-derived tet gene sequence (partial sequence) (4), and a λ phage-derived attL sequence (5) were each amplified by PCR. Fragment (1) was amplified using λ DNA as a template, and (1)f (SEQ ID NO: 9) and (1)r (SEQ ID NO: 10) as primers. Fragment (2) was amplified using chromosomal DNA of E. coli having Tn9 such as GM2159 and GM2150 as a template, and (2)f (SEQ ID NO: 11) and (2)r (SEQ ID NO: 12) as primers. Fragment (3) was amplified using T7 phage DNA as a template, and (3)f (SEQ ID NO: 13) and (3)r (SEQ ID NO: 14) as primers. Fragment (4) was amplified using pBR322 as a template, and (4)f (SEQ ID NO: 15) and (4)r (SEQ ID NO: 16) as primers. The fragment (5) was amplified using λ DNA as a template, and (5)f (SEQ ID NO: 17) and (5)r (SEQ ID NO: 18) as primers. The aforementioned GM2159 and GM2150 can be obtained from the E. coli Genetic Stock Center (Yale University, Dept. Biology, Osborn Memorial Labs., P.O. Box 6666, New Haven, Conn., U.S.A. 06511-7444).

Furthermore, a thr operon terminator sequence (58 bp) (6) was obtained by annealing synthetic DNAs (6)f (SEQ ID NO: 19) and (6)r (SEQ ID NO: 20).

Crossover PCR was performed using each of the obtained fragments as shown in Table 3 to obtain a DNA fragment (hereinafter, referred to as "fragment A") to which the fragments (1), (6), (2), (3), (4) and (5) were ligated.

TABLE 3

| Template | Primer | Fragment obtained |
|---|---|---|
| (1) and (6) | (1)f and (6)r2 | (1) + (6) |
| (2) and (3) | (2)f and (3)r | (2) + (3) |
| (4) and (5) | (4)f and (5)r | (4) + (5) |
| (1) + (6) and (2) + (3) | (1)f and (3)r | (1) + (6) + (2) + (3) |
| (1) + (6) + (2) + (3) and (4) + (5) | (1)f and (5)r | (1) + (6) + (2) + (3) + (4) + (5) |

Subsequently, the $P_L$ promoter sequence (SD sequence existing upstream from lacZ is added) was amplified by PCR using λ DNA as a template and a primer P1 (SEQ ID NO: 21) and P2mtr (including the mtr ORF sequence of 36 bp, SEQ ID NO: 22) or P2tnab (including the tnaB ORF sequence of 36 bp, SEQ ID NO: 23). Crossover PCR was performed using this amplified fragment and fragment A as templates and a primer (1)fmtr (SEQ ID NO: 24) or (1)ftnab (SEQ ID NO: 25) including a sequence (36 bp) of an upstream region of ORF of the mtr gene or the tnaB gene and the primer P2mtr or P2tnab. Each amplified fragment included a sequence of an upstream region of the mtr gene or the tnaB gene and an internal sequence of ORF of either gene at both ends. The nucleotide sequences of these DNA fragments are shown in SEQ ID NOS: 26 and 27. The structures of these DNA fragments are shown in Table 4.

TABLE 4

| Position in SEQ ID NO: 26 or 27 | Components |
|---|---|
| 1 to 36 | Upstream sequence of mtr gene or tnaB gene |
| 37 to 202 | attR of λ phage |
| 203 to 260 | thr operon terminator of E. coli K12 |
| 261 to 1043 | cat gene of Tn9 |
| 1043 to 1175 | Early gene promoter (Pa2) of T7 phage |
| 1176 to 1521 | tet gene sequence derived from pBR322 |
| 1522 to 1666 | attL of λ phage |
| 1671 to 1933 | $P_L$ promoter of λ phage |
| 1934 to 3178 or 3181 | mtr gene or tnaB gene |

Each of the above DNA fragments was introduced in a conventional manner into the TD-18 strain, which is a derivative of *E. coli* K-12 W3110 into which a helper plasmid pKD46 had been previously introduced. pKD46 is known to express Red recombinase (PNAS, 97(12), 6640-6645, 2000). After gene substitution occurred, the plasmid pKD46 was deleted from the transformants. Since the transformed strains into which each of the above DNA fragments has been introduced exhibit chloramphenicol resistance, the desired mtr gene or tnaB gene promoter-enhanced strain can be efficiently selected using this marker.

Then, the aforementioned mtr gene or tnaB gene promoter-enhanced strains were infected with P1 phage. Using each of the P1 phage-infected strains as a donor for P1 transduction, an upstream region of the mtr gene or tnaB gene ORF of L-phenylalanine-producing bacterium, AJ12741(R/GAL strain) was replaced with the $P_L$ promoter by P1 transduction by using chloramphenicol resistance as an index. It was confirmed by PCR that the desired gene substitution occurred.

<2> Production of L-phenylalanine by mtr Gene Promoter-enhanced Strain and tnaB Gene Promoter-enhanced Strain The R/GAL strain (RM11), in which an upstream region of the mtr gene ORF was replaced with the $P_L$ promoter, and the R/GAL strain (Rtp32), in which an upstream region of the tnaB gene ORF was replaced with the $P_L$ promoter, were obtained as described above. These bacterial strains were cultured in the same manner as in Example 1 to produce L-phenylalanine, and the amounts of L-phenylalanine and L-tryptophan in the medium were measured. The results are shown in Table 5.

TABLE 5

| Bacterial strain | L-Phe(g/L) | L-Trp(mg/L) |
| --- | --- | --- |
| R/GAL | 6.8 | 60 |
| RM11 | 6.9 | <1.5 |
| Rtp22 | 7.1 | <1.5 |

As shown in Table 5, the R/GAL strain produced L-tryptophan as a byproduct. However, the mtr promoter-enhanced strain RM11 and the tnaB promoter-enhanced strain Rtp32 did not produce L-tryptophan as a byproduct and accumulated L-phenylalanine in an amount comparable to that obtained with the R/GAL strain.

While the invention has been described in detail with reference to preferred embodiments thereof, it will be apparent to one skilled in the art that various changes can be made, and equivalents employed, without departing from the scope of the invention. Each of the aforementioned documents, as well as the foreign priority document, JP 2003-161181, is incorporated by reference herein in its entirety.

What is claimed is:

1. A method for producing a target substance selected from the group consisting of L-amino acids and nucleic acids comprising:
    (a) culturing an *Escherichia coli* bacterium which has an ability to produce the target substance in a medium, and
    (b) collecting the target substance from the medium,
    wherein said bacterium is modified so that a system for cell uptake of a byproduct of the target substance is enhanced.

2. The method according to claim 1, wherein said byproduct is selected from the group consisting of an intermediate in a biosynthetic pathway of said target substance, and a product of another biosynthesis system branching off from said pathway.

3. The method according to claim 1, wherein said target substance is L-phenylalanine and said byproduct is L-tryptophan.

4. The method according to claim 1, wherein said system for uptake of a byproduct is selected from the group consisting of Mtr and TnaB.

5. The method according to claim 4, wherein an activity of said system is increased by a method selected from the group consisting of
    (a) increasing a copy number of an mtr gene or tnaB gene, and
    (b) modifying an expression regulatory sequence of an mtr gene or tnaB gene.

6. The method according to claim 5, wherein said mtr gene comprises a DNA sequence selected from the group consisting of
    (a) the DNA sequence which encodes a protein sequence shown in SEQ ID No. 2,
    (b) the DNA sequence shown in SEQ ID No. 1, and
    (c) the DNA sequence which encodes a protein sequence having at least 90% homology to the sequence shown in SEQ ID No. 2,
    wherein said mtr gene encodes a protein which has the activity of a Mtr protein.

7. The method according to claim 5, wherein said tnaB gene comprises a DNA sequence selected from the group consisting of
    (a) the DNA sequence which encodes a protein sequence shown in SEQ ID No. 4,
    (b) the DNA sequence shown in SEQ ID No. 3, and
    (c) the DNA sequence which encodes a protein sequence having at least 90% homology to the sequence shown in SEQ ID No. 4,
    wherein said tnaB gene encodes a protein which has the activity of a TnaB protein.

* * * * *

SEQUENCE LISTING

<160> NUMBER OF SEQ ID NOS: 27

<210> SEQ ID NO 1
<211> LENGTH: 1550
<212> TYPE: DNA
<213> ORGANISM: Escherichia coli
<220> FEATURE:
<221> NAME/KEY: CDS
<222> LOCATION: (181)..(1425)

<400> SEQUENCE: 1

```
cgtcgtcgtt tcggtggtga tgcgtaatca tcgctgaaca gcgaacacaa tctgtaaaat      60
aatatataca gccccgattt ttaccatcgg ggcttttttt ctgtcttttg tactcgtgta     120
ctggtacagt gcaatgcata acaacgcagt cgcactattt ttcactggag agaagccctc     180 atg gca aca cta acc acc acc caa acg tca ccg tcg ctg ctt ggc ggc      228
Met Ala Thr Leu Thr Thr Thr Gln Thr Ser Pro Ser Leu Leu Gly Gly
1               5                   10                  15 gtg gtg att atc ggc ggc acc att att ggc gca ggg atg ttt tct ctg      276
Val Val Ile Ile Gly Gly Thr Ile Ile Gly Ala Gly Met Phe Ser Leu
            20                  25                  30 cca gtg gtc atg tcc ggg gcg tgg ttt ttc tgg tca atg gcg gcg ctg      324
Pro Val Val Met Ser Gly Ala Trp Phe Phe Trp Ser Met Ala Ala Leu
        35                  40                  45 atc ttt acc tgg ttc tgt atg ctg cat tcc ggc ttg atg att ctg gaa      372
Ile Phe Thr Trp Phe Cys Met Leu His Ser Gly Leu Met Ile Leu Glu
    50                  55                  60 gct aac ctg aat tac aga atc ggt tcg agt ttt gac acc atc acc aaa      420
Ala Asn Leu Asn Tyr Arg Ile Gly Ser Ser Phe Asp Thr Ile Thr Lys
65                  70                  75                  80 gat ttg ctg ggc aaa ggc tgg aac gtg gtc aac ggc att tcc att gcc      468
Asp Leu Leu Gly Lys Gly Trp Asn Val Val Asn Gly Ile Ser Ile Ala
                85                  90                  95 ttt gtg ctc tat atc ctg acc tat gcc tat att tct gcc agt ggt tcg      516
```

```
                Phe Val Leu Tyr Ile Leu Thr Tyr Ala Tyr Ile Ser Ala Ser Gly Ser
                                100                 105                 110 att ctg cat cac acc ttc gca gag atg tca cta aac gtc ccg gca cgg         564
Ile Leu His His Thr Phe Ala Glu Met Ser Leu Asn Val Pro Ala Arg
            115                 120                 125 gcg gcg ggt ttt ggt ttt gca ttg ctg gta gcg ttt gtg gtg tgg ttg         612
Ala Ala Gly Phe Gly Phe Ala Leu Leu Val Ala Phe Val Val Trp Leu
130                 135                 140 agc act aaa gcc gtc agt cgc atg aca gcg att gtg ctg ggg gcg aaa         660
Ser Thr Lys Ala Val Ser Arg Met Thr Ala Ile Val Leu Gly Ala Lys
145                 150                 155                 160 gtc att acc ttc ttc ctc acc ttt ggt agc ctg ctg ggg cat gtg cag         708
Val Ile Thr Phe Phe Leu Thr Phe Gly Ser Leu Leu Gly His Val Gln
            165                 170                 175 cct gcg aca ttg ttc aac gtc gcc gaa agc aat gcg tct tat gca ccg         756
Pro Ala Thr Leu Phe Asn Val Ala Glu Ser Asn Ala Ser Tyr Ala Pro
            180                 185                 190 tat ctg ttg atg acc ctg ccg ttc tgt ctg gca tcg ttt ggt tat cac         804
Tyr Leu Leu Met Thr Leu Pro Phe Cys Leu Ala Ser Phe Gly Tyr His
            195                 200                 205 ggt aac gtg cca agc ctg atg aag tat tac ggc aaa gat ccg aaa acc         852
Gly Asn Val Pro Ser Leu Met Lys Tyr Tyr Gly Lys Asp Pro Lys Thr
210                 215                 220 atc gtg aaa tgt ctg gtg tac ggt acg ctg atg gcg ctg gcg ctg tat         900
Ile Val Lys Cys Leu Val Tyr Gly Thr Leu Met Ala Leu Ala Leu Tyr
225                 230                 235                 240 acc atc tgg ttg ctg gcg acg atg ggt aac atc ccg cgt ccg gag ttt         948
Thr Ile Trp Leu Leu Ala Thr Met Gly Asn Ile Pro Arg Pro Glu Phe
                245                 250                 255 atc ggt att gca gag aag ggc ggt aat att gat gtg ctg gta cag gcg         996
Ile Gly Ile Ala Glu Lys Gly Gly Asn Ile Asp Val Leu Val Gln Ala
                260                 265                 270 tta agc ggc gta ctg aac agc cgt agt ctg gat ctg ctg ctg gtc gtg        1044
Leu Ser Gly Val Leu Asn Ser Arg Ser Leu Asp Leu Leu Leu Val Val
            275                 280                 285 ttc tca aac ttt gcg gta gcg agt tcg ttc ctc ggc gta acg ctg ggt        1092
Phe Ser Asn Phe Ala Val Ala Ser Ser Phe Leu Gly Val Thr Leu Gly
            290                 295                 300 ttg ttt gac tat ctg gca gat ctg ttt ggt ttc gac gac tcg gct gtg        1140
Leu Phe Asp Tyr Leu Ala Asp Leu Phe Gly Phe Asp Asp Ser Ala Val
305                 310                 315                 320 ggc cgc ttg aaa acg gca ttg ctg acc ttt gcc ccg cca gtt gtg ggg        1188
Gly Arg Leu Lys Thr Ala Leu Leu Thr Phe Ala Pro Pro Val Val Gly
                325                 330                 335 ggg ctg ttg ttc ccg aac gga ttc ctg tac gcc att ggt tat gct ggt        1236
Gly Leu Leu Phe Pro Asn Gly Phe Leu Tyr Ala Ile Gly Tyr Ala Gly
                340                 345                 350 tta gcg gct acc atc tgg gcg gca att gtt ccg gcg ctg tta gcc cgt        1284
Leu Ala Ala Thr Ile Trp Ala Ala Ile Val Pro Ala Leu Leu Ala Arg
            355                 360                 365 gca tcg cgt aaa cgc ttt ggc agc ccg aaa ttc cgc gtc tgg ggt ggc        1332
Ala Ser Arg Lys Arg Phe Gly Ser Pro Lys Phe Arg Val Trp Gly Gly
            370                 375                 380 aag ccg atg att gcg ctg att ctg gtg ttt ggc gtc ggc aac gca ctg        1380
Lys Pro Met Ile Ala Leu Ile Leu Val Phe Gly Val Gly Asn Ala Leu
385                 390                 395                 400 gtg cat att tta tcg agc ttt aat tta ctg ccg gtg tat cag taa            1425
Val His Ile Leu Ser Ser Phe Asn Leu Leu Pro Val Tyr Gln
                405                 410
```

```
tcagcggtgc cttatccgac atttctgctg cctacacaat gcctgatgcg cttcgcttat    1485
caggtctatg taggacagcg ttgccagctc ggataaggct tcccgcgtta agacacacta    1545
tccca                                                                1550
```

<210> SEQ ID NO 2
<211> LENGTH: 414
<212> TYPE: PRT
<213> ORGANISM: Escherichia coli

<400> SEQUENCE: 2

```
Met Ala Thr Leu Thr Thr Thr Gln Thr Ser Pro Ser Leu Leu Gly Gly
1               5                   10                  15

Val Val Ile Ile Gly Gly Thr Ile Ile Gly Ala Gly Met Phe Ser Leu
            20                  25                  30

Pro Val Val Met Ser Gly Ala Trp Phe Phe Trp Ser Met Ala Ala Leu
        35                  40                  45

Ile Phe Thr Trp Phe Cys Met Leu His Ser Gly Leu Met Ile Leu Glu
    50                  55                  60

Ala Asn Leu Asn Tyr Arg Ile Gly Ser Ser Phe Asp Thr Ile Thr Lys
65                  70                  75                  80

Asp Leu Leu Gly Lys Gly Trp Asn Val Val Asn Gly Ile Ser Ile Ala
                85                  90                  95

Phe Val Leu Tyr Ile Leu Thr Tyr Ala Tyr Ile Ser Ala Ser Gly Ser
            100                 105                 110

Ile Leu His His Thr Phe Ala Glu Met Ser Leu Asn Val Pro Ala Arg
        115                 120                 125

Ala Ala Gly Phe Gly Phe Ala Leu Leu Val Ala Phe Val Val Trp Leu
    130                 135                 140

Ser Thr Lys Ala Val Ser Arg Met Thr Ala Ile Val Leu Gly Ala Lys
145                 150                 155                 160

Val Ile Thr Phe Phe Leu Thr Phe Gly Ser Leu Leu Gly His Val Gln
                165                 170                 175

Pro Ala Thr Leu Phe Asn Val Ala Glu Ser Asn Ala Ser Tyr Ala Pro
            180                 185                 190

Tyr Leu Leu Met Thr Leu Pro Phe Cys Leu Ala Ser Phe Gly Tyr His
        195                 200                 205

Gly Asn Val Pro Ser Leu Met Lys Tyr Tyr Gly Lys Asp Pro Lys Thr
    210                 215                 220

Ile Val Lys Cys Leu Val Tyr Gly Thr Leu Met Ala Leu Ala Leu Tyr
225                 230                 235                 240

Thr Ile Trp Leu Leu Ala Thr Met Gly Asn Ile Pro Arg Pro Glu Phe
                245                 250                 255

Ile Gly Ile Ala Glu Lys Gly Gly Asn Ile Asp Val Leu Val Gln Ala
            260                 265                 270

Leu Ser Gly Val Leu Asn Ser Arg Ser Leu Asp Leu Leu Leu Val Val
        275                 280                 285

Phe Ser Asn Phe Ala Val Ala Ser Ser Phe Leu Gly Val Thr Leu Gly
    290                 295                 300

Leu Phe Asp Tyr Leu Ala Asp Leu Phe Gly Phe Asp Asp Ser Ala Val
305                 310                 315                 320

Gly Arg Leu Lys Thr Ala Leu Leu Thr Phe Ala Pro Pro Val Val Gly
                325                 330                 335

Gly Leu Leu Phe Pro Asn Gly Phe Leu Tyr Ala Ile Gly Tyr Ala Gly
            340                 345                 350
```

```
Leu Ala Ala Thr Ile Trp Ala Ala Ile Val Pro Ala Leu Leu Ala Arg
            355                 360                 365

Ala Ser Arg Lys Arg Phe Gly Ser Pro Lys Phe Arg Val Trp Gly Gly
        370                 375                 380

Lys Pro Met Ile Ala Leu Ile Leu Val Phe Gly Val Gly Asn Ala Leu
385                 390                 395                 400

Val His Ile Leu Ser Ser Phe Asn Leu Leu Pro Val Tyr Gln
                405                 410

<210> SEQ ID NO 3
<211> LENGTH: 1450
<212> TYPE: DNA
<213> ORGANISM: Escherichia coli
<220> FEATURE:
<221> NAME/KEY: CDS
<222> LOCATION: (91)..(1338)

<400> SEQUENCE: 3
ttaatactac agagtggcta aaggatgtt agccactctc ttaccctaca tcctcaataa        60
caaaaatagc cttcctctaa aggtggcatc atg act gat caa gct gaa aaa aag      114
                                 Met Thr Asp Gln Ala Glu Lys Lys
                                  1               5 cac tct gca ttt tgg ggt gtt atg gtt ata gca ggt aca gta att ggt      162
His Ser Ala Phe Trp Gly Val Met Val Ile Ala Gly Thr Val Ile Gly
         10                  15                  20 gga ggt atg ttt gct tta cct gtt gat ctt gcc ggt gcc tgg ttt ttc      210
Gly Gly Met Phe Ala Leu Pro Val Asp Leu Ala Gly Ala Trp Phe Phe
 25                  30                  35                  40 tgg ggt gcc ttt atc ctt atc att gcc tgg ttt tca atg ctt cat tcc      258
Trp Gly Ala Phe Ile Leu Ile Ile Ala Trp Phe Ser Met Leu His Ser
                 45                  50                  55 ggg tta ttg tta tta gaa gca aat tta aat tat ccc gtc ggc tcc agt      306
Gly Leu Leu Leu Leu Glu Ala Asn Leu Asn Tyr Pro Val Gly Ser Ser
             60                  65                  70 ttt aac acc atc acc aaa gat tta atc ggt aac acc tgg aac att atc      354
Phe Asn Thr Ile Thr Lys Asp Leu Ile Gly Asn Thr Trp Asn Ile Ile
         75                  80                  85 agc ggt att acc gtt gcc ttc gtc ctc tat atc ctc act tat gcc tat      402
Ser Gly Ile Thr Val Ala Phe Val Leu Tyr Ile Leu Thr Tyr Ala Tyr
 90                  95                 100 atc tct gct aat ggt gcg atc att agt gaa acg ata tca atg aat ttg      450
Ile Ser Ala Asn Gly Ala Ile Ile Ser Glu Thr Ile Ser Met Asn Leu
105                 110                 115                 120 ggt tat cac gct aat cca cgt att gtc ggg atc tgc aca gcc att ttc      498
Gly Tyr His Ala Asn Pro Arg Ile Val Gly Ile Cys Thr Ala Ile Phe
                125                 130                 135 gtt gcc agc gta ttg tgg tta agt tcg tta gcc gcc agt cgt att acc      546
Val Ala Ser Val Leu Trp Leu Ser Ser Leu Ala Ala Ser Arg Ile Thr
            140                 145                 150 tca ttg ttc ctc ggg ctg aag att atc tcc ttt gtg atc gtg ttt ggt      594
Ser Leu Phe Leu Gly Leu Lys Ile Ile Ser Phe Val Ile Val Phe Gly
            155                 160                 165 tct ttt ttc ttc cag gtc gat tac tcc att ctg cgc gac gcc acc agc      642
Ser Phe Phe Phe Gln Val Asp Tyr Ser Ile Leu Arg Asp Ala Thr Ser
        170                 175                 180 tcc act gcg gga acg tct tac ttc ccg tat atc ttt atg gct ttg ccg      690
Ser Thr Ala Gly Thr Ser Tyr Phe Pro Tyr Ile Phe Met Ala Leu Pro
185                 190                 195                 200 gtg tgt ctg gcg tca ttt ggt ttc cac ggc aat att ccc agc ctg att      738
```

```
Val Cys Leu Ala Ser Phe Gly Phe His Gly Asn Ile Pro Ser Leu Ile
            205                 210                 215 att tgc tat gga aaa cgc aaa gat aag tta atc aaa agc gtg gta ttt      786
Ile Cys Tyr Gly Lys Arg Lys Asp Lys Leu Ile Lys Ser Val Val Phe
            220                 225                 230 ggt tcg ctg ctg gcg ctg gtg att tat ctc ttc tgg ctc tat tgc acc      834
Gly Ser Leu Leu Ala Leu Val Ile Tyr Leu Phe Trp Leu Tyr Cys Thr
            235                 240                 245 atg ggg aat att ccg cga gaa agc ttt aag gcg att atc tcc tca ggc      882
Met Gly Asn Ile Pro Arg Glu Ser Phe Lys Ala Ile Ile Ser Ser Gly
            250                 255                 260 ggc aac gtt gat tcg ctg gtg aaa tcg ttc ctc ggc acc aaa cag cac      930
Gly Asn Val Asp Ser Leu Val Lys Ser Phe Leu Gly Thr Lys Gln His
265                 270                 275                 280 ggc att atc gag ttt tgc ctg ctg gtg ttc tct aac tta gct gtt gcc      978
Gly Ile Ile Glu Phe Cys Leu Leu Val Phe Ser Asn Leu Ala Val Ala
                285                 290                 295 agt tcg ttc ttt ggt gtc acg ctg ggg ttg ttc gat tat ctg gcg gac     1026
Ser Ser Phe Phe Gly Val Thr Leu Gly Leu Phe Asp Tyr Leu Ala Asp
            300                 305                 310 ctg ttt aag att gat aac tcc cac ggc ggg cgt ttc aaa acc gtg ctg     1074
Leu Phe Lys Ile Asp Asn Ser His Gly Gly Arg Phe Lys Thr Val Leu
            315                 320                 325 tta acc ttc ctg cca cct gcg ttg ttg tat ctg atc ttc ccg aac ggc     1122
Leu Thr Phe Leu Pro Pro Ala Leu Leu Tyr Leu Ile Phe Pro Asn Gly
            330                 335                 340 ttt att tac ggg atc ggc ggt gcc ggg ctg tgc gcc acc atc tgg gcg     1170
Phe Ile Tyr Gly Ile Gly Gly Ala Gly Leu Cys Ala Thr Ile Trp Ala
345                 350                 355                 360 gtc att att ccc gca gtg ctt gca atc aaa gct cgc aag aag ttt ccc     1218
Val Ile Ile Pro Ala Val Leu Ala Ile Lys Ala Arg Lys Lys Phe Pro
                365                 370                 375 aat cag atg ttc acg gtc tgg ggc ggc aat ctt att ccg gcg att gtc     1266
Asn Gln Met Phe Thr Val Trp Gly Gly Asn Leu Ile Pro Ala Ile Val
            380                 385                 390 att ctc ttt ggt ata acc gtg att ttg tgc tgg ttc ggc aac gtc ttt     1314
Ile Leu Phe Gly Ile Thr Val Ile Leu Cys Trp Phe Gly Asn Val Phe
            395                 400                 405 aac gtg tta cct aaa ttt ggc taa atccttcaag aagccagcca ttcgctggct   1368
Asn Val Leu Pro Lys Phe Gly
            410                 415 tcttgcctct caggaaatca cttatgtcca aatggcaact cgcctgatcc tccttcacca  1428
cgtatgcttt gcgtcacctt ac                                           1450

<210> SEQ ID NO 4
<211> LENGTH: 415
<212> TYPE: PRT
<213> ORGANISM: Escherichia coli

<400> SEQUENCE: 4

Met Thr Asp Gln Ala Glu Lys Lys His Ser Ala Phe Trp Gly Val Met
1               5                   10                  15

Val Ile Ala Gly Thr Val Ile Gly Gly Gly Met Phe Ala Leu Pro Val
                20                  25                  30

Asp Leu Ala Gly Ala Trp Phe Phe Trp Gly Ala Phe Ile Leu Ile Ile
            35                  40                  45

Ala Trp Phe Ser Met Leu His Ser Gly Leu Leu Leu Leu Glu Ala Asn
        50                  55                  60
```

```
Leu Asn Tyr Pro Val Gly Ser Ser Phe Asn Thr Ile Thr Lys Asp Leu
 65                  70                  75                  80

Ile Gly Asn Thr Trp Asn Ile Ile Ser Gly Ile Thr Val Ala Phe Val
                 85                  90                  95

Leu Tyr Ile Leu Thr Tyr Ala Tyr Ile Ser Ala Asn Gly Ala Ile Ile
            100                 105                 110

Ser Glu Thr Ile Ser Met Asn Leu Gly Tyr His Ala Asn Pro Arg Ile
        115                 120                 125

Val Gly Ile Cys Thr Ala Ile Phe Val Ala Ser Val Leu Trp Leu Ser
    130                 135                 140

Ser Leu Ala Ala Ser Arg Ile Thr Ser Leu Phe Leu Gly Leu Lys Ile
145                 150                 155                 160

Ile Ser Phe Val Ile Val Phe Gly Ser Phe Phe Gln Val Asp Tyr
                165                 170                 175

Ser Ile Leu Arg Asp Ala Thr Ser Ser Thr Ala Gly Thr Ser Tyr Phe
            180                 185                 190

Pro Tyr Ile Phe Met Ala Leu Pro Val Cys Leu Ala Ser Phe Gly Phe
            195                 200                 205

His Gly Asn Ile Pro Ser Leu Ile Ile Cys Tyr Gly Lys Arg Lys Asp
210                 215                 220

Lys Leu Ile Lys Ser Val Val Phe Gly Ser Leu Leu Ala Leu Val Ile
225                 230                 235                 240

Tyr Leu Phe Trp Leu Tyr Cys Thr Met Gly Asn Ile Pro Arg Glu Ser
                245                 250                 255

Phe Lys Ala Ile Ile Ser Ser Gly Gly Asn Val Asp Ser Leu Val Lys
            260                 265                 270

Ser Phe Leu Gly Thr Lys Gln His Gly Ile Ile Glu Phe Cys Leu Leu
        275                 280                 285

Val Phe Ser Asn Leu Ala Val Ala Ser Ser Phe Phe Gly Val Thr Leu
    290                 295                 300

Gly Leu Phe Asp Tyr Leu Ala Asp Leu Phe Lys Ile Asp Asn Ser His
305                 310                 315                 320

Gly Gly Arg Phe Lys Thr Val Leu Leu Thr Phe Leu Pro Pro Ala Leu
                325                 330                 335

Leu Tyr Leu Ile Phe Pro Asn Gly Phe Ile Tyr Gly Ile Gly Gly Ala
            340                 345                 350

Gly Leu Cys Ala Thr Ile Trp Ala Val Ile Ile Pro Ala Val Leu Ala
        355                 360                 365

Ile Lys Ala Arg Lys Lys Phe Pro Asn Gln Met Phe Thr Val Trp Gly
370                 375                 380

Gly Asn Leu Ile Pro Ala Ile Val Ile Leu Phe Gly Ile Thr Val Ile
385                 390                 395                 400

Leu Cys Trp Phe Gly Asn Val Phe Asn Val Leu Pro Lys Phe Gly
                405                 410                 415
```

<210> SEQ ID NO 5
<211> LENGTH: 30
<212> TYPE: DNA
<213> ORGANISM: artificial
<220> FEATURE:
<223> OTHER INFORMATION: primer

<400> SEQUENCE: 5
gggagctcgt cgtttcggtg gtgatgcgta     30

<210> SEQ ID NO 6
<211> LENGTH: 30
<212> TYPE: DNA
<213> ORGANISM: artificial
<220> FEATURE:
<223> OTHER INFORMATION: primer

<400> SEQUENCE: 6
ggggtaccga tagtgtgtct taacgcggga                              30

<210> SEQ ID NO 7
<211> LENGTH: 30
<212> TYPE: DNA
<213> ORGANISM: artificial
<220> FEATURE:
<223> OTHER INFORMATION: primer

<400> SEQUENCE: 7
gggtcgacgt tagccactct cttaccctac                              30

<210> SEQ ID NO 8
<211> LENGTH: 30
<212> TYPE: DNA
<213> ORGANISM: artificial
<220> FEATURE:
<223> OTHER INFORMATION: primer

<400> SEQUENCE: 8
ggctgcagcg caaagcatac gtggtgaagg                              30

<210> SEQ ID NO 9
<211> LENGTH: 18
<212> TYPE: DNA
<213> ORGANISM: artificial
<220> FEATURE:
<223> OTHER INFORMATION: primer (1)f

<400> SEQUENCE: 9
cgctcaagtt agtataaa                                           18

<210> SEQ ID NO 10
<211> LENGTH: 54
<212> TYPE: DNA
<213> ORGANISM: artificial
<220> FEATURE:
<223> OTHER INFORMATION: primer (1)r

<400> SEQUENCE: 10
cctgacagtg cgggcttttt ttttcgacca ctgcagtctg ttacaggtca ctaa   54

<210> SEQ ID NO 11
<211> LENGTH: 54
<212> TYPE: DNA
<213> ORGANISM: artificial
<220> FEATURE:
<223> OTHER INFORMATION: primer (2)f

<400> SEQUENCE: 11
cccgcactgt caggtgcggg cttttttctg tgttaagctt cgacgaattt ctgc   54

<210> SEQ ID NO 12
<211> LENGTH: 54
<212> TYPE: DNA
<213> ORGANISM: artificial
<220> FEATURE:
<223> OTHER INFORMATION: primer (2)r -continued

```
<400> SEQUENCE: 12
gcagcgtcaa ccgggcgctc tagctagata tcggatccga gattttcagg agct        54

<210> SEQ ID NO 13
<211> LENGTH: 54
<212> TYPE: DNA
<213> ORGANISM: artificial
<220> FEATURE:
<223> OTHER INFORMATION: primer (3)f

<400> SEQUENCE: 13
agctcctgaa aatctcggat ccgatatcta gctagagcgc cggttgacg ctgc         54

<210> SEQ ID NO 14
<211> LENGTH: 54
<212> TYPE: DNA
<213> ORGANISM: artificial
<220> FEATURE:
<223> OTHER INFORMATION: primer (3)r

<400> SEQUENCE: 14
ctacgcgatc atggcgacca cacccgtcct gtggatctcc ggataagtag acag        54

<210> SEQ ID NO 15
<211> LENGTH: 54
<212> TYPE: DNA
<213> ORGANISM: artificial
<220> FEATURE:
<223> OTHER INFORMATION: primer (4)f

<400> SEQUENCE: 15
ttcgtgcgac ttatcaggct gtctacttat ccggagatcc acaggacggg tgtg        54

<210> SEQ ID NO 16
<211> LENGTH: 54
<212> TYPE: DNA
<213> ORGANISM: artificial
<220> FEATURE:
<223> OTHER INFORMATION: primer (4)r

<400> SEQUENCE: 16
cgaattctca tgtttgacag cttatcatcg ataagcttta atgcggtagt ttat        54

<210> SEQ ID NO 17
<211> LENGTH: 54
<212> TYPE: DNA
<213> ORGANISM: artificial
<220> FEATURE:
<223> OTHER INFORMATION: primer (5)f

<400> SEQUENCE: 17
ttagcaattt aactgtgata aactaccgca ttaaagctta tcgatgataa gctg        54

<210> SEQ ID NO 18
<211> LENGTH: 54
<212> TYPE: DNA
<213> ORGANISM: artificial
<220> FEATURE:
<223> OTHER INFORMATION: primer (5)r

<400> SEQUENCE: 18
ttttgcaggg gggcattgtt tggtaggtga agatcttgaa gcctgctttt ttat        54

<210> SEQ ID NO 19
<211> LENGTH: 58
```

<212> TYPE: DNA
<213> ORGANISM: artificial
<220> FEATURE:
<223> OTHER INFORMATION: synthetic DNA (6)f

<400> SEQUENCE: 19
ctgcagtggt cgaaaaaaaa agcccgcact gtcaggtgcg ggctttttc tgtgttaa        58

<210> SEQ ID NO 20
<211> LENGTH: 58
<212> TYPE: DNA
<213> ORGANISM: artificial
<220> FEATURE:
<223> OTHER INFORMATION: synthetic DNA (6)r

<400> SEQUENCE: 20
ttaacacaga aaaagcccg cacctgacag tgcgggcttt tttttcgac cactgcag         58

<210> SEQ ID NO 21
<211> LENGTH: 54
<212> TYPE: DNA
<213> ORGANISM: artificial
<220> FEATURE:
<223> OTHER INFORMATION: primer P1

<400> SEQUENCE: 21
tgccaactta gtataaaaaa gcaggcttca agatcttcac ctaccaaaca atgc           54

<210> SEQ ID NO 22
<211> LENGTH: 72
<212> TYPE: DNA
<213> ORGANISM: artificial
<220> FEATURE:
<223> OTHER INFORMATION: primer P2mtr

<400> SEQUENCE: 22
cgacggtgac gtttgggtgg tggttagtgt tgccatagcc tgtttccttc tagacggcca    60
atgcttcgtt tc                                                         72

<210> SEQ ID NO 23
<211> LENGTH: 72
<212> TYPE: DNA
<213> ORGANISM: artificial
<220> FEATURE:
<223> OTHER INFORMATION: primer P2tnab

<400> SEQUENCE: 23
aaatgcagag tgcttttttt cagcttgatc agtcatagcc tgtttccttc tagacggcca    60
atgcttcgtt tc                                                         72

<210> SEQ ID NO 24
<211> LENGTH: 54
<212> TYPE: DNA
<213> ORGANISM: artificial
<220> FEATURE:
<223> OTHER INFORMATION: primer (1)fmtr

<400> SEQUENCE: 24
gcgaacacaa tctgtaaaat aatatataca gccccgcgct caagttagta taaa           54

<210> SEQ ID NO 25
<211> LENGTH: 54
<212> TYPE: DNA
<213> ORGANISM: artificial
<220> FEATURE:

<223> OTHER INFORMATION: primer (1)ftnab

<400> SEQUENCE: 25
tcctcaataa caaaaatagc cttcctctaa aggtggcgct caagttagta taaa        54

<210> SEQ ID NO 26
<211> LENGTH: 3178
<212> TYPE: DNA
<213> ORGANISM: Artificial Sequence
<220> FEATURE:
<223> OTHER INFORMATION: fused gene

<400> SEQUENCE: 26

| | |
|---|---|
| gcgaacacaa tctgtaaaat aatatataca gccccgcgct caagttagta taaaaaagct | 60 |
| gaacgagaaa cgtaaaatga tataaatatc aatatattaa attagatttt gcataaaaaa | 120 |
| cagactacat aatactgtaa aacacaacat atgcagtcac tatgaatcaa ctacttagat | 180 |
| ggtattagtg acctgtaaca gactgcagtg gtcgaaaaaa aaagcccgca ctgtcaggtg | 240 |
| cgggcttttt tctgtgttaa gcttcgacga atttctgcca ttcatccgct tattatcact | 300 |
| tattcaggcg tagcaccagg cgtttaaggg caccaataac tgccttaaaa aaattacgcc | 360 |
| ccgccctgcc actcatcgca gtactgttgt aattcattaa gcattctgcc gacatggaag | 420 |
| ccatcacaga cggcatgatg aacctgaatc gccagcggca tcagcacctt gtcgccttgc | 480 |
| gtataatatt tgcccatggt gaaaacgggg gcgaagaagt tgtccatatt ggccacgttt | 540 |
| aaatcaaaac tggtgaaact cacccaggga ttggctgaga cgaaaaacat attctcaata | 600 |
| aaccctttag ggaaataggc caggttttca ccgtaacacg ccacatcttg cgaatatatg | 660 |
| tgtagaaact gccggaaatc gtcgtggtat tcactccaga gcgatgaaaa cgtttcagtt | 720 |
| tgctcatgga aaacggtgta acaagggtga acactatccc atatcaccag ctcaccgtct | 780 |
| ttcattgcca tacggaattc cggatgagca ttcatcaggc gggcaagaat gtgaataaag | 840 |
| gccggataaa acttgtgctt attttttcttt acggtcttta aaaaggccgt aatatccagc | 900 |
| tgaacggtct ggttataggt acattgagca actgactgaa atgcctcaaa atgttcttta | 960 |
| cgatgccatt gggatatatc aacggtggta tatccagtga ttttttttctc catttttagct | 1020 |
| tccttagctc ctgaaaatct cggatccgat atctagctag agcgcccggt tgacgctgct | 1080 |
| agtgttacct agcgatttgt atcttactgc atgttacttc atgttgtcaa tacctgtttt | 1140 |
| tcgtgcgact tatcaggctg tctacttatc cggagatcca caggacgggt gtggtcgcca | 1200 |
| tgatcgcgta gtcgatagtg gctccaagta gcgaagcgag caggactggg cggcggccaa | 1260 |
| agcggtcgga cagtgctccg agaacgggtg cgcatagaaa ttgcatcaac gcatatagcg | 1320 |
| ctagcagcac gccatagtga ctggcgatgc tgtcggaatg gacgatatcc cgcaagaggc | 1380 |
| ccggcagtac cggcataacc aagcctatgc ctacagcatc cagggtgacg gtgccgagga | 1440 |
| tgacgatgag cgcattgtta gatttcatac acggtgcctg actgcgttag caatttaact | 1500 |
| gtgataaact accgcattaa agcttatcga tgataagctg tcaaacatga gaattcgaaa | 1560 |
| tcaaataatg atttatttt gactgatagt gacctgttcg ttgcaacaaa ttgataagca | 1620 |
| atgcttttt ataatgccaa cttagtataa aaaagcaggc ttcaagatct tcacctacca | 1680 |
| aacaatgccc cctgcaaaa aataaattca tataaaaaac atacgataa ccatctgcgg | 1740 |
| tgataaatta tctctggcgg tgttgacata ataccactg gcggtgatac tgagcacatc | 1800 |
| agcaggacgc actgaccacc atgaaggtga cgctcttaaa aattaagccc tgaagaaggg | 1860 |
| cagcattcaa agcagaaggc tttggggtgt gtgatacgaa acgaagcatt ggccgtctag | 1920 |

```
aaggaaacag gctatggcaa cactaaccac cacccaaacg tcaccgtcgc tgcttggcgg    1980
cgtggtgatt atcggcggca ccattattgg cgcagggatg ttttctctgc cagtggtcat    2040
gtccggggcg tggttttct ggtcaatggc ggcgctgatc tttacctggt tctgtatgct    2100
gcattccggc ttgatgattc tggaagctaa cctgaattac agaatcggtt cgagttttga    2160
caccatcacc aaagatttgc tgggcaaagg ctggaacgtg gtcaacggca tttccattgc    2220 cttgtgctc tatatcctga cctatgccta tatttctgcc agtggttcga ttctgcatca    2280
caccttcgca gagatgtcac taaacgtccc ggcacgggcg gcgggttttg gttttgcatt    2340
gctggtagcg tttgtggtgt ggttgagcac taaagccgtc agtcgcatga cagcgattgt    2400 gctggggcg aaagtcatta ccttcttcct cacctttggt agcctgctgg ggcatgtgca    2460
gcctgcgaca ttgttcaacg tcgccgaaag caatgcgtct tatgcaccgt atctgttgat    2520
gaccctgccg ttctgtctgg catcgtttgg ttatcacggt aacgtgccaa gcctgatgaa    2580
gtattacggc aaagatccga aaccatcgt gaaatgtctg gtgtacggta cgctgatggc    2640
gctggcgctg taccatctg gttgctggc gacgatgggc aacatcccgc gtccggagtt    2700
tatcggtatt gcagagaagg gcggtaatat tgatgtgctg gtacaggcgt taagcggcgt    2760
actgaacagc cgtagtctgg atctgctgct ggtcgtgttc tcaaactttg cggtagcgag    2820
ttcgttcctc ggcgtaacgc tgggtttgtt tgactatctg gcagatctgt ttggtttcga    2880
cgactcggct gtgggccgct tgaaaacggc attgctgacc tttgccccgc cagttgtggg    2940
ggggctgttg ttcccgaacg gattcctgta cgccattggt tatgctggtt tagcggctac    3000
catctgggcg gcaattgttc cggcgctgtt agcccgtgca tcgcgtaaac gctttggcag    3060
cccgaaattc cgcgtctggg gtggcaagcc gatgattgcg ctgattctgg tgtttggcgt    3120
cggcaacgca ctggtgcata ttttatcgag ctttaattta ctgccggtgt atcagtaa     3178
```

<210> SEQ ID NO 27
<211> LENGTH: 3181
<212> TYPE: DNA
<213> ORGANISM: Artificial Sequence
<220> FEATURE:
<223> OTHER INFORMATION: fused gene

<400> SEQUENCE: 27

```
tcctcaataa caaaaatagc cttcctctaa aggtggcgct caagttagta taaaaaagct    60
gaacgagaaa cgtaaaatga tataaatatc aatatattaa attagatttt gcataaaaaa    120
cagactacat aatactgtaa aacacaacat atgcagtcac tatgaatcaa ctacttagat    180
ggtattagtg acctgtaaca gactgcagtg gtcgaaaaaa aaagcccgca ctgtcaggtg    240
cgggcttttt tctgtgttaa gcttcgacga atttctgcca ttcatccgct tattatcact    300
tattcaggcg tagcaccagg cgtttaaggg caccaataac tgccttaaaa aaattacgcc    360
ccgccctgcc actcatcgca gtactgttgt aattcattaa gcattctgcc gacatggaag    420
ccatcacaga cggcatgatg aacctgaatc gccagcggca tcagcacctt gtcgccttgc    480
gtataatatt tgcccatggt gaaaacgggg gcgaagaagt tgtccatatt ggccacgttt    540
aaatcaaaac tggtgaaact cacccaggga ttggctgaga cgaaaaacat attctcaata    600
aaccctttag ggaaataggc caggttttca ccgtaacacg ccacatcttg cgaatatatg    660
tgtagaaact gccggaaatc gtcgtggtat tcactccaga gcgatgaaaa cgtttcagtt    720
tgctcatgga aaacggtgta acaagggtga acactatccc atatcaccag ctcaccgtct    780
```

-continued

```
ttcattgcca tacggaattc cggatgagca ttcatcaggc gggcaagaat gtgaataaag    840
gccggataaa acttgtgctt attttctttt acggtcttta aaaaggccgt aatatccagc    900
tgaacggtct ggttataggt acattgagca actgactgaa atgcctcaaa atgttcttta    960
cgatgccatt gggatatatc aacggtggta tatccagtga ttttttctc cattttagct   1020 tccttagctc ctgaaaatct cggatccgat atctagctag agcgcccggt tgacgctgct   1080
agtgttacct agcgatttgt atcttactgc atgttacttc atgttgtcaa tacctgtttt   1140
tcgtgcgact tatcaggctg tctacttatc cggagatcca caggacgggt gtggtcgcca   1200
tgatcgcgta gtcgatagtg gctccaagta gcgaagcgag caggactggg cggcggccaa   1260
agcggtcgga cagtgctccg agaacgggtg cgcatagaaa ttgcatcaac gcatatagcg   1320
ctagcagcac gccatagtga ctggcgatgc tgtcggaatg gacgatatcc cgcaagaggc   1380
ccggcagtac cggcataacc aagcctatgc ctacagcatc cagggtgacg gtgccgagga   1440
tgacgatgag cgcattgtta gatttcatac acggtgcctg actgcgttag caatttaact   1500
gtgataaact accgcattaa agcttatcga tgataagctg tcaaacatga gaattcgaaa   1560
tcaaataatg atttatttt gactgatagt gacctgttcg ttgcaacaaa ttgataagca   1620 atgcttttt ataatgccaa cttagtataa aaaagcaggc ttcaagatct tcacctacca   1680
aacaatgccc ccctgcaaaa aataaattca tataaaaaac atacagataa ccatctgcgg   1740
tgataaatta tctctggcgg tgttgacata ataccactg gcggtgatac tgagcacatc   1800
agcaggacgc actgaccacc atgaaggtga cgctcttaaa aattaagccc tgaagaaggg   1860
cagcattcaa agcagaaggc tttggggtgt gtgatacgaa acgaagcatt ggccgtctag   1920
aaggaaacag gctatgactg atcaagctga aaaaaagcac tctgcatttt ggggtgttat   1980
ggttatagca ggtacagtaa ttggtggagg tatgtttgct ttacctgttg atcttgccgg   2040
tgcctggttt ttctggggtg cctttatcct tatcattgcc tggttttcaa tgcttcattc   2100
cgggttattg ttattagaag caaatttaaa ttatcccgtc ggctccagtt ttaacaccat   2160
caccaaagat ttaatcggta acacctggaa cattatcagc ggtattaccg ttgccttcgt   2220
tctctatatc ctcacttatg cctatatctc tgctaatggt gcgatcatta gtgaaacgat   2280
atcaatgaat ttgggttatc acgctaatcc acgtattgtc gggatctgca cagccatttt   2340
cgttgccagc gtattgtggt taagttcgtt agccgccagt cgtattacct cattgttcct   2400
cgggctgaag attatctcct ttgtgatcgt gtttggttct ttttcttcc aggtcgatta   2460 ctccattctg cgcgacgcca ccagctccac tgcgggaacg tcttacttcc cgtatatctt   2520
tatggctttg ccggtgtgtc tggcgtcatt tggtttccac ggcaatattc ccagcctgat   2580
tatttgctat ggaaaacgca agataagtt aatcaaaagc gtggtatttg gttcgctgct   2640
ggcgctggtg atttatctct tctggctcta ttgcaccatg gggaatattc cgcgagaaag   2700
ctttaaggcg attatctcct caggcggcaa cgttgattcg ctggtgaaat cgttcctcgg   2760
caccaaacag cacggcatta tcgagttttg cctgctggtg ttctctaact agctgttgc   2820 cagttcgttc tttggtgtca cgctggggtt gttcgattat ctggcggacc tgtttaagat   2880
tgataactcc cacggcgggc gtttcaaaac cgtgctgtta accttcctgc cacctgcgtt   2940
gttgtatctg atcttcccga acggcttat ttacgggatc ggcggtgccg ggctgtgcgc   3000
caccatctgg gcggtcatta ttcccgcagt gcttgcaatc aaagctcgca agaagtttcc   3060
caatcagatg ttcacggtct ggggcggcaa tcttattccg gcgattgtca ttctctttgg   3120
```

```
tataaccgtg attttgtgct ggttcggcaa cgtctttaac gtgttaccta aatttggcta    3180
a                                                                    3181
```